(12) United States Patent
Grillberger et al.

(10) Patent No.: US 10,527,551 B2
(45) Date of Patent: Jan. 7, 2020

(54) METHOD OF PREDICTING A PERFORMANCE CHARACTERISTIC OF A PLANT OR YEAST HYDROLYSATE AND ITS USE

(71) Applicants: BAXALTA INCORPORATED, Bannockburn, IL (US); BAXALTA GMBH, Zug (CH)

(72) Inventors: Leopold Grillberger, Vienna (AT); Renata Baldaszti-Juric, Gross-Enzersdorf (AT); Wolfgang Langer, Vienna (AT); Manfred Reiter, Vienna (AT)

(73) Assignees: Baxalta Incorporated, Bannockburn, IL (US); Baxalta GmbH, Zug (CH)

(*) Notice: Subject to any disclaimer, the term of this patent is extended or adjusted under 35 U.S.C. 154(b) by 596 days.

(21) Appl. No.: 15/108,592

(22) PCT Filed: Dec. 18, 2014

(86) PCT No.: PCT/EP2014/078559
§ 371 (c)(1),
(2) Date: Jun. 28, 2016

(87) PCT Pub. No.: WO2015/101510
PCT Pub. Date: Jul. 9, 2015

(65) Prior Publication Data
US 2016/0327484 A1    Nov. 10, 2016

Related U.S. Application Data

(60) Provisional application No. 61/921,756, filed on Dec. 30, 2013.

(51) Int. Cl.
*G01N 21/64* (2006.01)
*C12N 5/00* (2006.01)
*C12N 7/00* (2006.01)

(52) U.S. Cl.
CPC ....... *G01N 21/6486* (2013.01); *C12N 5/0018* (2013.01); *C12N 7/00* (2013.01); *G01N 2021/6419* (2013.01); *G01N 2201/1293* (2013.01)

(58) Field of Classification Search
CPC .................................................. G01N 21/6486
USPC ......................................................... 702/19
See application file for complete search history.

(56) References Cited

FOREIGN PATENT DOCUMENTS

| WO | WO 1996/015231 A2 | 5/1996 |
|---|---|---|
| WO | WO 1996/026266 A1 | 8/1996 |
| WO | WO 1998/015614 A1 | 4/1998 |
| WO | WO 2000/003000 A2 | 1/2000 |
| WO | WO 2001/023527 A1 | 4/2001 |
| WO | WO 2004/005493 A1 | 1/2004 |
| WO | WO 2006/045438 A1 | 5/2006 |
| WO | WO 2010/132731 A1 | 11/2010 |
| WO | WO 2012/059520 A1 * | 5/2012 |

OTHER PUBLICATIONS

Franěk, František, et al., "Plant Protein Hydrolysates: Preparation of Defined Peptide Fractions Promoting Growth and Production in Animal Cells Cultures" Biotechnology Progress v. 16, n. 5, pp. 688-692 (2000).

José, Gledson E., et al., "Predicting mab product yields from cultivation media components, using near-infrared and 2D-fluorescence spectroscopies", Biotechnology Prog., v. 27, n. 5, pp. 1339-1346 (2011).

Lee, Hae Woo, et al., "Data Fusion-Based Assessment of Raw Materials in Mammalian Cell Culture", Biotechnology and Bioengineering, v. 109, n. 11, Nov. 2012.

* cited by examiner

*Primary Examiner* — Jerry Lin

(57) ABSTRACT

The present invention relates to a method of predicting a performance characteristic of a plant or yeast hydrolysate, wherein a plant or yeast hydrolysate sample is measured with 2D fluorescence spectroscopy in powder form. Said method comprises the steps for providing a model based on a predetermined value of a manufacturing parameter of interest. For this purpose a training set consisting of predetermined manufacturing parameter of interest (e.g volumetric productivity parameter, virus titer or cell number) and fluorescence spectroscopic data is used. The fluorescence spectroscopic data is correlated to the values of the manufacturing parameter of interest to obtain a calibration model/model parameters by applying multivariate data analysis. This calibration model is being used to predict the manufacturing parameter of interest for new samples dedicated for the manufacturing process. This prediction is used for a decision to accept or reject the lot which corresponds to the respective sample for use in the manufacturing process or for further evaluation depending on the pre-defined range of the manufacturing parameter of interest. The invention further relates to a method for preparation of a cell culture medium, preferably an animal protein free cell culture medium, a method for cultivating cells, a method for producing a recombinant target protein, a method for producing an immunogenic composition, whereby the above method of predicting a performance characteristic has been used for selecting the plant or yeast hydrolysate to be used in the manufacturing process.

12 Claims, 1 Drawing Sheet

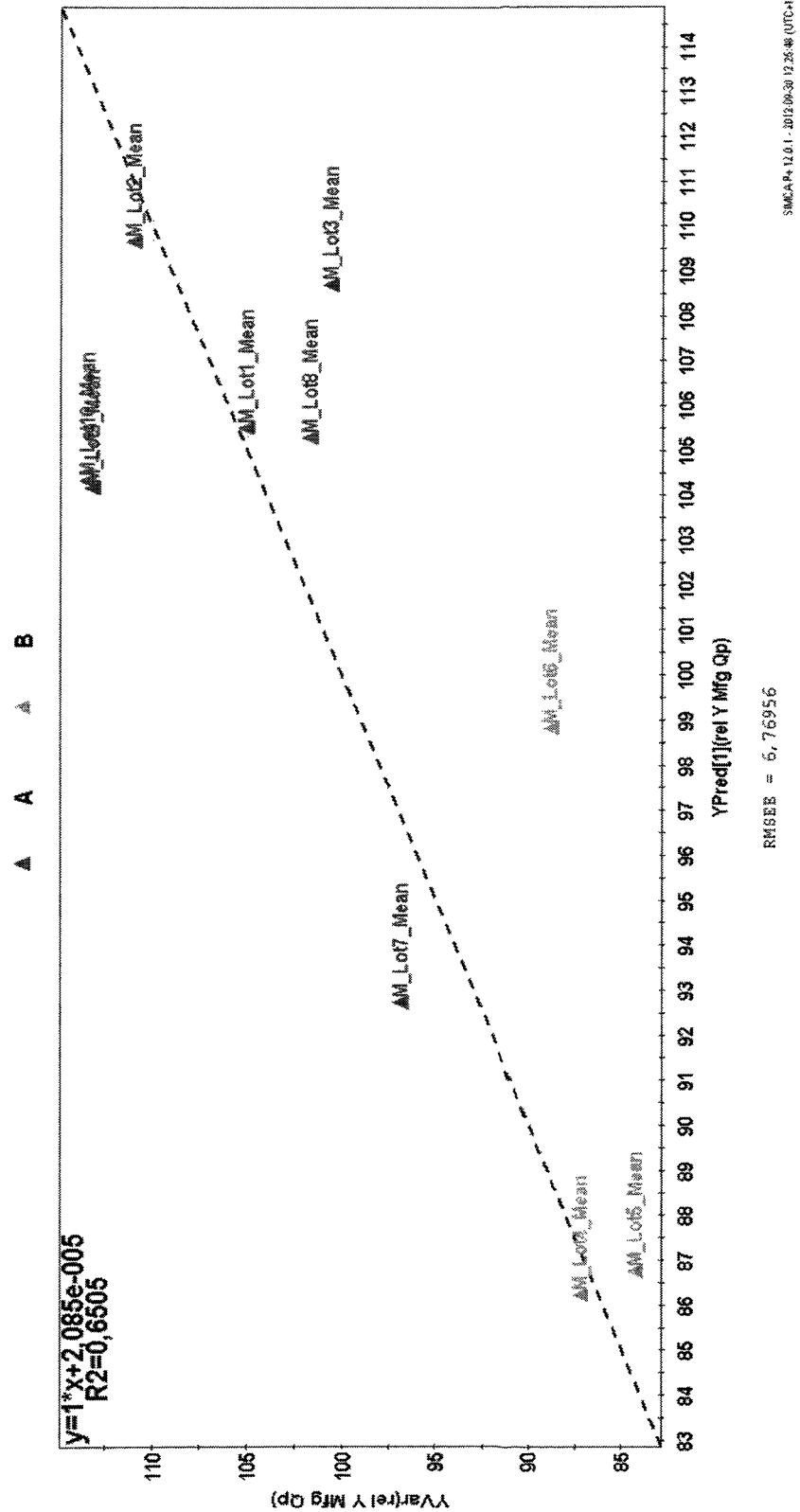

METHOD OF PREDICTING A PERFORMANCE CHARACTERISTIC OF A PLANT OR YEAST HYDROLYSATE AND ITS USE

FIELD OF THE INVENTION

The present invention relates to a method of predicting a performance characteristic of a plant or yeast hydrolysate measured in powder form. Said method comprises the steps for providing a model based on a predetermined value of a manufacturing parameter of interest. For this purpose a training set is used and the obtained data from said training set is correlated to the manufacturing parameter of interest by determining, e.g. fluorescence spectroscopic data; performing a multivariante data analysis of said data to obtain model parameters correlating the measured value determined of the sample with the corresponding predetermined manufacturing parameters of interest. Said model is then used to obtain information correlated to the manufacturing parameter of interest of a new sample different from the samples of the training set and obtaining predictive information related to the performance characteristic of the sample by determining whether said manufacturing parameter of interest falls into a predetermined range. Further, the invention relates to a method for preparation of a cell culture medium, preferably an animal protein free cell culture medium, a method for cultivating cells, a method for producing a recombinant target protein and a method for producing an immunogenic composition comprising a virus or virus antigen, wherein all methods utilize the method of predicting a performance characteristic of a plant or yeast hydrolysate measured in powder form.

BACKGROUND OF THE INVENTION

For cultivation of cells, particularly eukaryotic cells, and more specifically mammalian cells, there is a constant need to use special cell culture media that provide nutrient substances that are required for efficient growth of the cells and for the production of the recombinant proteins or an immunogenic composition comprising a virus or virus antigen. For the efficient production of biological products, such as viruses or recombinant proteins, it is important that an optimal cell density is achieved as well as the protein expression itself is increased to obtain maximum product yield.

Cell culture media formulations have been supplemented with a range of additives in the past, including undefined components like fetal calf serum (FCS), several animal derived proteins and/or protein hydrolysates of bovine origin.

In general, serum or serum-derived substances, such as albumin, transferrin or insulin, may contain unwanted agents that can contaminate the cell cultures and the biological products obtained there from. Furthermore, human serum derived additives have to be tested for all known viruses, including hepatitis and HIV, that can be transmitted by serum. Moreover, bovine serum and products derived there from bear the risk of BSE contamination. In addition, all serum-derived products can be contaminated by unknown constituents. In the case of serum or protein additives that are derived from human or other animal sources in cell culture, there are numerous problems (e.g. the varying quality in composition of the different batches and the risk of contamination with mycoplasma, viruses or BSE), particularly if the cells are used for production of drugs or vaccines for human administration.

Therefore, many attempts have been made to provide efficient host systems and cultivation conditions, which do not require serum or other animal protein compounds. Simple serum free medium typically includes basal medium, vitamins, amino acids organic or inorganic salts, and optionally additional components to make the medium nutritionally complex.

Plant or yeast hydrolysates are known to be useful for fermentation processes and can enhance the growth of many fastidious organisms, yeasts and fungi. WO 96/26266 describes that gluten hydrolysate can be used in tissue culture. Franek et al. (Biotechnology Progress (2000) 16, 688-692) describe growth and productivity promoting effects of defined soy hydrolysate peptide fractions.

WO 96/15231 discloses a serum-free medium composed of the synthetic minimal essential medium and yeast extract for propagation of vertebrate cells and virus production process. A medium formulation composed of a basal cell culture medium comprising a rice peptide and an extract of yeast and enzymatic digest thereof, and/or a plant lipid for growth of animal cells is disclosed in WO 98/15614. WO 00/03000 discloses a medium that comprises a soy hydrolysate and a yeast extract, but also requires the presence of recombinant forms of animal proteins, such as growth factors.

WO 01/23527 discloses a medium for the animal protein-free and serum-free cultivation of cells, especially mammalian cells, whereby the medium contains soy hydrolysate.

However, since plant and yeast hydrolysates are natural products, the quality of commercially available lots of these plant or yeast hydrolysates varies extremely. The quality differs dependent on the growth, maturity and harvest of the starting plants or yeast. Of course, for plant hydrolysates also those features are dependent from the area of cultivation, in particular climate-induced variations. Further, the different suppliers in the market use different manufacturing processes and also the products of a single supplier vary from lot-to-lot.

In large scale cell culture one can observe that, even if, there seems to be no difference in the quality of different commercially available lots of those hydrolysates by regular means of quality control, like e.g. the given specification of the producer, there is a considerable difference in the performance of the hydrolysate with respect to cell growth, protein expression rates and virus propagation, respectively, when these hydrolysates are used as supplements of basal cell culture media. As a result, there are large variations in the production of recombinant proteins or viral products as a function of the quality of lots of plant or yeast hydrolysates, in particular soy hydrolysates used ("lot-to-lot variation") as a supplement of basal cell culture media or as a component of a cell culture medium.

To solve this problem, WO 2006/045438 discloses a "plant or yeast hydrolysate reduced" medium in order to obtain more consistent characteristics in the respective media due to lower plant or yeast hydrolysate contents. Such media comprise a reduced amount of plant or yeast hydrolysate in combination with polyamines, Nevertheless, even in those "plant or yeast hydrolysate reduced" media the performance differences based on the lot-to-lot variation of those hydrolysates are still considerable. In this context the term "lot" means a production batch provided by a specific manufacturer, wherein the mass and volume, respectively, can vary from manufacturer to manufacturer. In case of soy hydrolysate a lot is several tons.

In order to determine the performance of a plant or yeast hydrolysate in advance, the respective lots of said hydrolysate are used in a small scale cell culture process/test ("use test") prior to the use in large scale process. Only lots having a high performance characteristic in the small scale cell culture tests are used later on in large scale processes.

Such small scale cell culture tests are very time consuming and cost intensive due to the need of laboratory resources. For instance, about six weeks are needed to perform the cell culture tests and analysis thereof, involving about twenty staff members in laboratory. Due to this time consuming small scale cell culture tests for performance evaluation of the plant or yeast hydrolysate, it is not possible to purchase only high performing lots from the supplier. After a six week evaluation time, normally, the supplier has already sold all lots under investigation. For a large scale biotechnological campaign involving, e.g. a 6000 liter fermenter more than one lot is required. Therefore, normally a few lots have to be purchased and stored while performing the small scale cell culture tests. The low performing lots are not used in large scale processes because of the risk of failure. However, the costs for purchasing these lots have already been arisen. In addition, in most cases the low performing lots have to be disposed of which also raises significant costs and wastes natural resources.

Even if, small scale cell culture tests will also be necessary in the future in order to exclude the presence of inhibitory components in those plant or yeast hydrolysates etc., there is a need for a fast pre-screening method for performance prediction of a given plant or yeast hydrolysate lot to avoid or at least significantly reduce the number of small scale cell culture processes/tests in order to save time and resources.

In order to analyze lot-to-lot variability in raw materials like protein or yeast hydrolysates José et al. (Biotechnol. Prog., 2011, Vol. 27, No.5, pages 1339 to 1346) combined near and mid infrared spectroscopy with two-dimensional (2D)-fluorescence spectroscopy. For that reason an aqueous solution of a specific peptone as raw material was analyzed in comparison to a defined aqueous chemical media containing multiple components. As a result it was found that 2D-fluorescence spectroscopy alone was only suitable to analyze and/or predict the performance of a defined chemical media. Moreover, the 2D-fluorescence spectra of the tested raw materials could only be weakly correlated with the actual measured performance in cell culture media. The authors concluded that only a combination of these methods can be used for performance prediction.

Non-published experiments showed that 2D-fluorescence spectroscopy measurements of aqueous solutions of plant or yeast hydrolysate samples showed no significant differences in different samples which could be correlated to certain production performance characteristics, manufacturing parameters or productivity parameters.

Surprisingly, it was found that when the 2D-fluorescence spectroscopy measurements of powder samples of the respective plant or yeast hydrolysates were taken, the resulting spectra showed great signal strength as well as broad variation of signals. What is even more beneficial is that no time consuming sample preparation is needed, e.g. preparing an aqueous solution of the respective plant or yeast hydrolysate followed by sterilization. Further, the amount of plant or yeast hydrolysate material used for the method according to the invention can be immensely reduced by a factor of about 20 to about 50 in comparison to the prior art measurements using aqueous solutions of the respective plant or yeast hydrolysate samples. Therefore, e.g. a small amount of soy hydrolysate powder from a lot can be used as a sample to predict the performance of the whole lot.

Furthermore, these 2D-fluorescence spectroscopy results of a given plant or yeast hydrolysate sample, in particular derived from a plant or yeast hydrolysate lot, could be correlated with manufacturing data of a protein when produced in a cell culture medium comprising an amount of said plant or yeast hydrolysate lot.

A benefit of the invention is also the fact that there is no need to combine various spectral analysis methods as described in the prior art.

SUMMARY OF THE INVENTION

An object of the present invention is to provide a method of predicting a performance characteristic of a plant or yeast hydrolysate, wherein a plant or yeast hydrolysate sample is measured with 2D fluorescence spectroscopy in powder form. Preferably the plant or yeast hydrolysate sample, in particular a soy hydrolysate sample, is an amount of plant or yeast hydrolysate of a commercially purchased lot. Said method comprises the steps for providing a model based on a predetermined value of a manufacturing parameter of interest.

For this purpose a training set consisting of predetermined manufacturing parameter of interest (e.g volumetric productivity parameter, virus titer or cell number) and fluorescence spectroscopic data is used. The fluorescence spectroscopic data is correlated to the values of the manufacturing parameter of interest to obtain a calibration model/model parameters by applying multivariate data analysis. This calibration model is being used to predict the manufacturing parameter of interest for new samples dedicated for the manufacturing process. This prediction is used for a decision to accept or reject the lot which corresponds to the respective sample for use in the manufacturing process or for further evaluation depending on the pre-defined range of the manufacturing parameter of interest.

A further object of the present invention is to provide a method for preparation of a cell culture medium, preferably an animal protein free cell culture medium, a method for cultivating cells, a method for producing a recombinant target protein, a method for producing an immunogenic composition, whereby the above method of predicting a performance characteristic has been used for selecting the plant or yeast hydrolysate to be used in the manufacturing process.

The method according to the invention can be used e.g. as pre-screening method having the following advantages in comparison to small scale cell culture tests.

The method of predicting a performance characteristic according to the invention is a fast evaluation process, wherein the respective samples are measured in powder form. Therefore, only a minimum of sample preparation is required for analysis. The method is non-invasive meaning not destructive. After the pre-screening, i.e. after having finalized the method according to the invention the hydrolysate powder can be stored as retain sample or used for other applications or tests. The method follows the requirements of FDA's PAT (process analytical technology) initiative and can easily implemented into biotechnological and pharmaceutical processes underlying regulatory prerequisites. Further benefits of the invention have already been described at the end of the background section.

In addition, the method according to the invention can be performed within several minutes or hours. Based on those pre-screening results and the determined performance of a sample of the lot, it can be decided whether or not to purchase the lot and to "dedicate" it for appropriate cell culture applications or processes. In case of a low performing lot, there is no need any longer to purchase the whole lot that results in enormous inventory savings. Further, in case of a high performing lot the storage costs until the lot is "released" based on the data of time intensive cell culture tests can be tremendously reduced. A further benefit is that for this quick pre-screening analysis a small aliquot of plant or yeast hydrolysate powder, in particular soy hydrolysate powder, is sufficient.

Well-suited samples of plant or yeast hydrolysates can be selected based on the predicted performance characteristic in order to use only high performing plant or yeast hydrolysates in cell culture, in particular in large scale cell culture, in order to increase the yield of expressed recombinant protein or any other expression product or immunogenic composition and to provide an optimal cell culture medium for production of biological products, such as those used as pharmaceuticals or vaccines for therapeutic purposes.

Therefore, the method of predicting a performance characteristic of a plant or yeast hydrolysate according to the invention is favorable compared to expensive and time consuming cell culture tests and processes and reduces the need of small scale cell culture tests. This method is able to distinguish clearly between high and low performing hydrolysate samples and lots, which is of a great financial interest.

BRIEF DESCRIPTION OF THE DRAWING

FIG. 1 shows a plot for the predictive power of OPLS model (selected spectra, centered) calculated with data from the training data set obtained by the codes for the calculated mean values of the fluorescence data, which were used for further modeling.

DETAILED DESCRIPTION OF THE INVENTION

One aspect of the present invention relates to a method of predicting a performance characteristic of a plant or yeast hydrolysate, wherein a plant or yeast hydrolysate sample is measured with 2D fluorescence spectroscopy in powder form comprising the steps of
a) providing a training set comprising a plurality of plant or yeast hydrolysate samples, each sample having a predetermined value of a manufacturing parameter of interest,
b) irradiating a sample of said training set with light of a plurality of wavelengths in a predetermined range,
c) determining at least one measured value indicative of radiation emitted from the sample,
d) repeating steps b) and c) for all samples of said training set,
e) performing multivariate data analysis of the at least one measured value determined for each of the plurality of samples and corresponding predetermined manufacturing parameters of interest to obtain model parameters correlating the at least one measured value determined for each of the plurality of samples with the corresponding predetermined manufacturing parameters of interest,
f) obtaining information correlated to the manufacturing parameter of interest of a new sample different from the samples of said training set from an at least one measured value indicative of radiation emitted from the sample according to step c) after irradiating said sample according to step b) by using those model parameters obtained in step e),
g) obtaining predictive information related to the performance characteristic of the new sample by determining whether said manufacturing parameter of interest falls into a predetermined range.

In the method of the present invention the term "performance characteristic" means the performance of a plant or yeast hydrolysate in cell culture processes when added to the culture medium as a nutrient. In this respect a "performance" means that e.g. cells in cell culture produce a specific amount of protein per cell or per volume based on the used plant or yeast hydrolysate for the cell culture medium.

The term "plant hydrolysate" refers to any hydrolysates from plants, in particular it is selected from the group consisting of soy hydrolysate and wheat hydrolysate. In a preferred embodiment soy hydrolysate is used. The plant and yeast hydrolysate may be an ultrafiltered hydrolysate, a purified hydrolysate or crude hydrolysate.

The plant or yeast hydrolysate in the method according to the invention is used in powder form. In a preferred embodiment a soy hydrolysate powder is used in all methods according to the invention. In this respect "powder" means fine particles of any dry substance consisting of ground, pulverized, or otherwise finely dispersed solid particles.

The term "hydrolysate" includes any enzymatic or acidic digest of a vegetable or yeast extract. Preferably, hydrolysates according to the present invention are commercially available hydrolysates.

The "training set" according to the invention comprises a plurality of plant or yeast hydrolysate samples, preferably soy hydrolysate samples. Each sample has a predetermined value of a manufacturing parameter of interest. Said predetermined value of a manufacturing parameter has been determined in small scale cell culture tests or manufacturing runs prior to the start of establishing the model of the present invention.

The "manufacturing parameter of interest" may be determined on the basis of a cell culture and is selected from the group consisting of the volumetric productivity parameter, the virus titer and the cell number.

In the method according to the invention a least a sample, preferably all samples, of said training set is/are irradiated with light of a plurality of wavelengths in a predetermined range, preferably the wavelengths of light lies within a range of 290 to 550 nm. Further, at least one measured value indicative of radiation emitted from the sample and the samples, respectively, is determined, wherein irradiating and determining is preferably repeated for all samples of said training set. Preferably step b) and step c) of the method according to the invention comprise a two dimensional (2D) multiwavelength fluorescence spectroscopy analysis of the plant or yeast hydrolysate powder, preferably of the soy hydrolysate powder.

Fluorescence spectroscopy is a type of electromagnetic spectroscopy that analyses fluorescence from a sample and is known to the skilled person as a routine method. It involves using a beam of light, usually ultraviolet light that excites the electrons in molecules of certain compounds and causes them to emit light. Two-dimensional (2D) means that both excitation as well as emission wavelengths can be varied. The measurement result comprises a series of emission spectra, each emission spectrum obtained for an excitation wavelength of a plurality of predetermined excitation wavelengths. The measurement result may be arranged in a 2D matrix containing detailed information about the sample.

The 2D-multiwavelength fluorescence spectroscopy analysis may comprise at least the following steps:
- providing a sample of the plant or yeast hydrolysate powder, preferably soy hydrolysate;
- introducing a probe into the plant or yeast hydrolysate powder sample, preferably the soy hydrolysate in order to measure the fluorescence within the sample and
- recording of a 2D-multiwavelength fluorescence spectrum of said sample.

2D multi-wavelength fluorescence spectroscopic analysis may be carried out with e.g. the system BioView® comprising a sensor as well as a probe being able to perform measurement in plant or yeast hydrolysate powders that is available from Delta in Denmark. In all methods according to the invention a probe is put directly into the plant or yeast hydrolysate powder, preferably the soy hydrolysate powder. The powder may be within a tube that can be protected from light in a dark vessel in order to maintain the quality of the powder as good as possible. In order to perform the fluorescence spectroscopic analysis a probe adapter can be used to fix the sensor, e.g. the BioView sensor, at a defined height.

In a preferred embodiment the fluorescence probe comprises spectral filters adapted to measure fluorescence at defined wavelength combinations for excitation and emission wavelengths. The range of the wavelengths comprises ultraviolet and visible light (total wavelength range of 200 to 800 nanometers), mostly preferred in the range of 290 and 590 nanometers. To measure a 2D-multiwavelength fluorescence spectrum, excitation and emission wavelengths increase over the existing wavelength range, mostly preferred in 20 nanometer steps, providing a plurality of wavelength combinations.

The data acquisition may be carried out with standard techniques. When a BioView® sensor is used, fluorescence measurements are carried out, i.e. recorded, in a sampling mode of the accompanying BioView data acquisition software program. These measurements are referred to as "measured X" data.

In addition to the "measured X" data of each measurement a corresponding manufacturing parameter of interest may be recorded. Preferably the manufacturing parameter of interest is the volumetric productivity parameter of a plant or yeast hydrolysate, most preferably the volumetric productivity parameter of a soy hydrolysate. Those recorded parameters corresponding to the measurements are referred to as "process Y" data.

The manufacturing parameter of interest may be indicative of relative volumetric productivity of recombinant protein, the virus titer and the cell number. The volumetric productivity value of the manufacturing parameter of interest reflects an average of over hundred daily data points from several campaigns from different cell culture lines indicative of an average performance.

In one embodiment of the invention the method can comprise a data pre-processing. For data preprocessing the "measured X" data sets, e.g the fluorescence data, may be combined with corresponding "process Y" data sets that are obtained from the predetermined manufacturing parameter of interest of the plant or yeast hydrolysate, preferably the soy hydrolysate, to form one multivariate data set.

The combined data set may be subject to data preprocessing. In a preferred embodiment the arithmetic mean of the "measured X" data is calculated and combined with at least one manufacturing parameter of interest, e.g. the volumetric productivity parameter, virus titer or the cell number of the "process Y" data. In a preferred embodiment the "measured X" data sets are determined in the range of 310 nm to 590 nm. Further, in the "measured X" data sets wavelength values of interest may be selected based on biomedical indicators. In this way the amount of "measured X" data sets is reduced.

In another embodiment according to the invention a wavelength selection may be performed, e.g. a series of wavelengths used in fluorescence measurements has been reduced from 150 to 120. The wavelength selection may be based on the following rationale. According to fermentation experiments in bioreactors, where e.g. the BioView system may be used for monitoring, theses signals do not seem to reflect any biogenic fluorophores as vitamins or amino acids. They more likely indicate the measurement environment as the surface of the container or catching up of environmental light. Wavelength series that are determined without spectral filters for excitation or emission may therefore not used and therefore the wavelengths may be selected.

In addition, the reduced "measured X" data sets and/or the "process Y" data sets may be subject to scaling. In this process the reduced "measured X" data sets may be centered. Univariate scaling may be applied to the corresponding "process Y" data sets. Univariate scaling standardizes data sets measured in different units and/or ranges to a common range In one embodiment of the invention the invention may further comprise the step of performing data processing of the at least one measured value determined for each of the plurality of samples to obtain processed values, and using said processed values to perform multivariate data analysis in step e) according to the process of the present invention. In this respect the term "data pre-processing" according to the invention means that at least a wavelength selection or a scaling is performed, preferably both.

According to the invention the preprocessed or unprocessed "measured X" data sets together with the preprocessed or unprocessed "process Y" data sets may be subjected to further data processing. This data processing includes as a first aspect the quality of the source data that is assessed by statistical methods. Statistical methods such as ANOVA, Nested ANOVA, or General Linear Model or projection methods as Principal Components Analysis (PCA) or Independent Component Analysis (ICA) may be applied and are known to the skilled person in the art.

Basically, with these methods the preprocessed data sets may be reduced and their quality may be assessed in a reduced data space. As an example, the first principal component of preprocessed "measured X" data, also called $t_1$ values, is analyzed to evaluate the statistical significance of the measured data.

For example, values of the first principal component of preprocessed "measured X" data are entered into statistical software, mostly preferred is the statistical software program Minitab, available from Minitab Inc. in the USA. In a nested ANOVA model, for example, variance of said values is evaluated concerning statistical significance of measured material lots rather compared to the measurement setup (repetition of measurement: measuring 3 tubes containing powder of the same plant or yeast hydrolysate, preferably soy hydrolysate sample) and random correlation.

In one example, a possibly nested ANOVA model shows that the overwhelming majority of the variance of the first principal component, that is about 90%, are caused by different lots, whereas only about 10% are caused by the tube.

In one embodiment of the invention the method according to the invention further comprises in step e) performing data processing and multivariante data analysis that is performed according to a validated chemometric model.

According to step g) of the method according to the invention, predictive information can be obtained related to the performance characteristic of the new sample by determining whether said manufacturing parameter of interest falls into a predetermined range, said method comprises the following steps:
(i) setting an acceptable performance of a predetermined value of a manufacturing parameter of interest to be 100%, and
(ii) determining whether the determined manufacturing parameter of interest obtained after step f) is greater than 100% or not, wherein a performance of greater than 100% is a high performance and a performance of less than 100% is a low performance.

In step e) according to the method of the present invention a model is built. A model of the processed data may consist of finding a hyper plane approximating the processed data according to predetermined criteria (e.g. maximizing covariance), for instance. The distance of a sample to the approximating hyper plane may then be used as a predictive measure. For instance a PLS (Partial Least Squares) model may be built from processed "measured X" data and processed "process Y" data with the data analysis software SIMCA P+, available from Umetrics Inc. in the USA.

For instance, FIG. 1 shows the Observed versus Prediction plots that demonstrate the predictive power of the PLS (Partial Least Squares) model.

After model establishing, the model may be optionally further refined. In a first step, outliers and unusual data, i.e. data that deviate from accustomed values, may be removed from the raw model. In a second step, "VIPs" may be calculated from processed data sets in the SIMCA P+software and evaluated. VIP values reflect the importance of terms in the model both with respect to process Y (i.e. the manufacturing parameter of interest), i.e. its correlation to all the responses and with respect to X (in this example: wavelength combination). VIP variables may be selected by restricting the range of process Y values (i.e. manufacturing parameter of interest).

The following effects are achieved by the second step. Excluding noise in fluorescence data by removing fluorescence variables with lower correlation to the process Y data. Decreasing the risk of over-fitting of the model, i.e. the nature of spectral data is high correlation between the spectra. Hence, only the most fitting fluorescence variables concerning the manufacturing Y may be used for modeling.

By sequentially applying a model to new data sets for prediction the model robustness may be increased.

As a re-modelling step a new model may be determined using a predetermined number of VIP variables to achieve a further refinement. VIP variables may be selected by restricting the range of process Y values, i.e. the manufacturing parameter of interest.

The re-modelling process can be followed by model validation, wherein the predictive power of the selected model may be evaluated.

In routine use the fluorescence spectra of at least one new plant or yeast hydrolysate, preferably soy hydrolysate powder lot is measured. The fluorescence and manufacturing data are put into the SIMCA P+ software as "prediction set" or as predetermined manufacturing parameter of interest.

By using the "VIP"-Model and fluorescence data of the new data of the plant or yeast hydrolysate powder lot in the SIMCA P+ software, the process Y data, i.e. manufacturing parameter of interest, is calculated.

Based on the predicted result the lot corresponding to the investigated sample is released for further applications. Based on the predicted values a pre-selection or assessment of the appropriate application of the plant or yeast hydrolysate, preferably soy hydrolysate, may be done leading to the benefits of the present invention as described above. Of course, additional testing in appropriate small scale cell culture cultivations may also be carried out in order to minimize the risk in manufacturing due to e.g. toxic inorganic impurities that can not evaluated in fluorescence spectroscopy.

In another aspect of the invention, it is preferred that the validated chemometric model is calculated on the basis of the data as received from a pre-processing step further comprising the calculation of a chemometric model, the evaluation of said chemometric model, optionally the remodeling of the chemometric model by using specifically selected VIP-variables and the validation of the chemometric model with a new fluorescence data set obtainable from 2D-multiwavelength fluorescence analysis of a plant or yeast hydrolysate, preferably soy hydrolysate which performance is to be predicted.

In a further embodiment, the data pre-processing may comprise as a minimum the following two steps, i.e. Fluorescence data export and data alignment, in which fluorescence data and manufacturing data (including the manufacturing parameters of interest) are combined in one multivariate data set.

In a further preferred embodiment the arithmetic mean of the fluorescence signals is calculated and aligned to at least one manufacturing parameter of interest of a plant or yeast hydrolysate, preferably soy hydrolysate, e.g. the volumetric productivity, virus titer or the cell number; preferably the volumetric productivity and most preferably the volumetric productivity of soy hydrolysate.

The finalization of the multivariate data set is done by wavelength selection and scaling. For scaling various algorithms may be applied, partially depending on the data itself and the software that is used for chemometric modeling. In a preferred embodiment centering of fluorescence data and univariate scaling of manufacturing parameters of interest is applied.

After scaling statistical methods as ANOVA, nested ANOVA, or General Linear Model or projection methods as Principal Components Analysis (PCA) or Independent Component Analysis (ICA) are applied to evaluate the quality of the 2D-fluorescence data itself.

In a preferred embodiment first a PCA model of the fluorescence data is developed. Afterwards the "results" of the PCA model in the SIMCA P+ software are entered into a statistical software, mostly preferred is the software Minitab. In a nested ANOVA model variance of fluorescence data based on t-values is evaluated concerning statistical significance of measured material lots rather compared to the measurement setup (repetition of measurement: measuring 3 tubes containing powder of the same plant or yeast hydrolysate sample) and random correlation.

A chemometric model is calculated on the basis of the data as received from the pre-processing step further correlating the x-variables, i.e. in this case fluorescence values, to the process Y, i.e. manufacturing parameter of interest. For calculating chemometric model various algorithms can be applied. The most common linear modeling techniques are projection methods as principal component analysis (PCA), or principal component regression, or partial least squares (PLS) regression, or orthogonal partial least squares regression which is mostly preferred. Non-linear chemometric modeling techniques can be applied using neural networks or hybride modeling.

Purchasable software as MATLAB and its toolboxes (e.g. Eigenvector), Unscrambler and SIMCA tools can be used for modeling as well as any free available software. In a preferred embodiment SIMCA P+ and its features for linear modeling techniques are used to develop an OPLS model using fluorescence data for predicting of one manufacturing parameter of interest.

The evaluation of said chemometric model is based on specified attributes for model quality as regression coefficient ($R^2$) and the root mean square error of estimation as a minimum.

In a preferred embodiment the predictive power ($R^2$ of regression line in plot "observed versus predicted"), model stability (Q2Y) and most significant regression (p-value) at comparable data fit (R2Y) are assessed to ensure feasibility of the built model for prediction and avoiding model overfitting which leads to losses in robustness of the model (e.g. increasing predictive power by increasing the number of principal components, but risk of failure during model validation).

Optionally the remodeling of the OPLS-model is done by using specifically selected VIP-variables wherein VIP values reflect the importance of terms in the model both with respect to process Y, i.e. manufacturing parameter of interest, i.e. its correlation to all the responses, and with respect to X (=wavelength combination).

Finally, the validation of the chemometic model can be performed with a new fluorescence data set obtainable from 2D-multiwavelength fluorescence analysis of a plant or yeast hydrolysate, preferably soy hydrolysate that was not used for model building. The validation comprises the following steps:

Prediction of the manufacturing parameter of interest (=process Y) based on the fluorescence data,
Comparison of predicted process Y to process Y off-line analytically measured during the manufacturing process, and
Calculating the root mean square error of prediction.

Selection of manufacturing parameters of interest and rating of determined parameter depend on the manufacturing process where the described method is applied for performance prediction. However, the determined manufacturing parameter of interest is rated mainly based on business and financial reasons. The required minimum and maximum level or amount of the manufacturing parameter is defined in the associated product specification. Manufacturing experience leads to an adaption of an operating range for routine production where consistent manufacturing at a high performance level can be assured. Well-suited samples of the respective plant or yeast hydrolysate, preferably soy hydrolysate, are chosen on the basis of said rated determined manufacturing parameter of interest for model building and model validation.

The above-described method of predicting a performance characteristic according to the present invention may be comprised by all known cell culture processes, wherein plant or yeast hydrolysates, preferably soy hydrolysates, are used as component of the cell culture medium.

Thus, in another aspect of the invention, the invention further relates to a method for preparing a cell culture medium comprising the steps of:

aa) providing a plant or yeast hydrolysate having a high performance characteristic as determined by a method according to the invention and bb) mixing the hydrolysate of step aa) with other cell culture medium components to form the cell culture medium or adding the plant or yeast hydrolysate of step aa) to a basal cell culture medium to form the cell culture medium.

In another aspect of the invention, the invention further relates to a method for cultivating cells, comprising the steps of:

aa) providing a plant or yeast hydrolysate having a high performance characteristic as determined by a method according to the invention,
bb) mixing the hydrolysate of step aa) with other cell culture medium components to form the cell culture medium or adding the plant or yeast hydrolysate of step aa) to a basal cell culture medium to form the cell culture medium,
cc) providing one or more cells that produce a recombinant target protein,
dd) culturing the one or more cells in the plant or yeast hydrolysate supplemented cell culture medium, preferably a basal cell culture medium, to form a cell culture.

In another aspect of the invention, the invention further relates to a method for producing a recombinant target protein, comprising the steps of:

aa) providing a plant or yeast hydrolysate having a high performance characteristic as determined by a method according to the invention,
bb) mixing the hydrolysate of step aa) with other cell culture medium components to form the cell culture medium or adding the plant or yeast hydrolysate of step aa) to a basal cell culture medium to form a cell culture medium,
cc) providing one or more cells that produce a recombinant target protein,
ee) culturing the one or more cells in the plant or yeast hydrolysate supplemented cell culture medium, preferably a basal cell medium, such that a recombinant target protein is expressed and excreted from the cells into a culture supernatant, and recovering said target protein.

In addition, the target protein may be isolated, optionally purified and formulated, preferably formulated as a medicament.

In a preferred embodiment the basal medium can be supplemented with additional components that enhance the expression of a recombinant target protein such as polyamines.

In another aspect of the invention, the invention further relates to a method for producing an immunogenic composition comprising a virus or virus antigen, wherein the method comprises the steps of:

aa) providing a plant or yeast hydrolysate having a high performance characteristic as determined by a method according to the invention and
bb) mixing the hydrolysate of step aa) with other cell culture medium components to form the cell culture medium or adding the plant or yeast hydrolysate of step aa) to a basal cell culture medium to form a cell culture medium,
ff) providing a culture of cells,
gg) infecting the cells with a virus;
hh) incubating the infected cells to propagate the virus;
jj) harvesting the virus or virus antigen produced; and
kk) preparing an immunogenic composition from the harvested virus or virus antigen.

In addition, the harvested virus or virus antigen may be isolated, optionally purified prior to the preparation of the immunogenic composition. Preferably the immunogenic composition is used as a medicament and therefore formulated as a medicament.

In all methods according to the invention, the cells are selected from the group consisting of mammalian cells, insect cells, avian cells, bacterial cells, and yeast cells. The cells may be for example stem cells or recombinant cells transformed with a vector for recombinant gene expression, or cells transfected with a virus for producing viral products. The cells may also be for example cells producing a protein of interest. The cells may also be for example primary cells, e.g. chicken embryo cells, or primary cell lines. Preferred are cells that are used for in vitro virus production. In a preferred embodiment the cells may be BSC cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK-21 cells, CHO cells, NS-1 cells, MRC-5 cells, WI-38 cells, BHK cells, 293 cells, RK cells, and chicken embryo cells. In a preferred embodiment the cells are CHO cells or VERO cells.

In a preferred embodiment the cell/target protein combination is selected from the group consisting of CHO cells/coagulation factor VIII, factor VII, factor IX, factor II and factor X.

In all embodiments of the invention, the cell/virus combination is selected from the group consisting of Vero cell/attenuated vaccinia, Vero cell/vaccinia, Vero cell/hepatitis A, Vero cell/influenza virus, Vero cell/West Nile virus, Vero cell/SARS virus, and chicken embryo cells/FSME virus, chicken embryo cells/MVA, chicken embryo cells/recombinant MVA, avian cells/FSME virus, avian cells/MVA and avian cells/recombinant MVA.

The method according to the invention is used for preparation of a cell culture medium, preferably an animal protein free cell culture medium, comprising at least one of said plant or yeast hydrolysate, preferably soy hydrolysate having a high performance characteristic.

The cells used according to the present invention may be cultivated by a method selected from the group of batch-cultivation, feed-batch-cultivation, perfusion cultivation and chemostat-cultivation all of which are generally known in the field.

The nucleic acid sequence comprising a sequence coding for the target protein may be a vector. The vector may be a virus or a plasmid. The sequence coding for a target protein may be a specific gene or a biological functional part thereof. In a preferred embodiment the target protein is at least a biologically active part of a blood coagulation factor such as the Factor VIII.

Preferably, the nucleic acid further comprises other sequences suitable for controlled expression of a target protein such as promotor sequences, enhancers, TATA boxes, transcription initiation sites, polylinkers, restriction sites, poly-A-sequences, protein processing sequences, selection markers, and the like which are generally known to the person skilled in the art.

Most preferred are the following cell lines transformed with a recombinant vector for the expression of the respective products: CHO cells for the production of recombinant coagulation factor VIII, factor VII, factor IX, factor II and factor X.

The present invention further relates to a method for producing a virus or part of a virus, comprising the steps of:
providing a culture of cells that have been grown in an animal protein-free cell culture medium using a plant or yeast hydrolysate having a high performance characteristic as determined by the method according to the invention; and
infecting the cells with a virus;
selecting the virus-infected cells; and
incubating the cells to propagate the virus.

Further, the virus or virus antigen product produced is isolated, optionally purified and formulated, preferably as a medicament.

In a preferred embodiment the animal protein-free cell culture medium comprises at least one polyamine and a plant- and/or yeast-derived hydrolysate, preferably soy hydrolysate.

The virus used in the method according to the invention may be any pathogenic virus, mammalian, preferably human virus, such as a vaccinia or attenuated vaccinia virus, e.g. for smallpox vaccines, coronavirus, preferably SARS virus, e.g. for production of SARS vaccines, orthomyoxyvirus, preferably influenza virus, e.g. for production of influenza vaccines, paramyxovirus, retrovirus, influenza A or B virus, Ross River virus, flavivirus, preferably West Nile virus or FSME virus (i.e. tick borne encephalitis virus), e.g. for the production of the respective vaccines, picornavirus, arena virus, herpesvirus, poxvirus or adenovirus.

The virus may be a wild-type-virus, an attenuated virus, a reassortant virus, or a recombinant virus or combinations thereof, e.g. attenuated and recombinant. In addition, instead of actual virions being used to infect cells with a virus, an infectious nucleic acid clone may be used. Split virions may also be used.

The cells used for the method for producing a virus may be selected from the group consisting of mammalian cells, insect cells, avian cells, bacterial cells, and yeast cells.

Preferably, the cells are cultivated by a method selected from the group consisting of batch-cultivation, feed-batch-cultivation, perfusion cultivation and chemostat-cultivation.

Preferred combinations of cells with viruses for producing a virus or part of a virus are Vero cell/attenuated vaccinia, Vero cell/Vaccinia, Vero cell/Hepatitis A, Vero cell/Influenza Virus, Vero cell/West Nile Virus, Vero cell/SARS Virus, chicken embryo cells/FSME virus, chicken embryo cells/MVA, chicken embryo cells/recombinant MVA, avian cells/FSME virus, avian cells/MVA and avian cells/recombinant MVA.

The present invention further relates to a method of using a cell culture medium, preferably a animal protein-free cell culture medium, comprising at least one of said plant or yeast hydrolysates having a high performance characteristic as determined by a method according to the invention for culturing cells expressing a target protein.

In another aspect of the invention, the invention relates to the use of the method according to the invention for preparation of a cell culture medium, preferably an animal protein free cell culture medium, comprising at least one of said plant or yeast hydrolysate, preferably soy hydrolysate, having a high performance characteristic as determined by the method according to the invention.

The present invention will now be further illustrated in the following examples, without being limited thereto.

EXAMPLE

As an example a method of predicting the volumetric productivity parameter of a soy hydrolysate powder is established comprising the following steps.

Sample Preparation:

Commercially purchased soy hydrolysate powder, such as e.g. purchased from DOMO having the lot numbers 10310455, 10343630, 10328845, 10356200, 10122613, 10124440, 10161295, 10161564, 10343627, 10370308, 10371479 and 10371480, is put into a tube and the tube is put into a centrifuge beaker to darken it. In order to irradiate a sample of the training set with light of a plurality of wavelengths in a predetermined range, a probe that is able to measure the samples in powder form is used. Such a probe was purchased at BioView. Such BioView probe is put into tube and the probe is fixed at a defined height.

Training set Preparation:

A number of soy hydrolysate lots in powder form and their corresponding predetermined volumetric productivity of clotting data of a recombinant protein are used as samples. For this purpose the soy hydrolysate lots are divided into two sub-groups reflecting types of soy hydrolysate manufacturing process itself. The determined value of the volumetric productivity parameter which is in the present case the manufacturing parameter of interest reflects an average of >100 daily data points from several campaigns from different cell lines and, therefore, reflects this average performance irrespective from other influencing variables, as e.g.: cell lines, other raw materials, test system variation etc.

Steps Applied for 2D Mulitwavelength Fluorescence Measurements with the BioView Sensor:

The 2D multiwavelength fluorescence measurement is performed by a computer equipped with the BioView software belonging to the respective BioView probe. The parameters for measurement (gain=900, repetitions=3, sensitivity=high, measurement interval=continuously) are entered into the system and the measurement is performed with 10 data points for each measurement run followed by determination of the respective data set by the BioView software.

Data Pre-processing:

The data obtained from the BioView software that is the rough fluorescence data set is exported to the excel software using the BioView software. For this purpose mean values out of 10 data points are calculated in Excel. Then, all fluorescence data sets of all powder lots are exported in one file. In addition, the manufacturing parameter of interest, in the present example the volumetric productivity parameter of soy hydrolysate is entered as Y value (process Y) into the excel file. The complete data set, i.e. fluorescence data set and process Y is imported to the SIMCA P+ software followed by wavelength selection, centering and scaling of all data performed by SIMCA P+ software. The following scaling algorithms are applied as an example, the centering of the fluorescence data and an univariate scaling for the relative volumetric productivity parameters (process Y).

Calculation of Mean Values out of Fluorescence Data Measured in 3 Tubes Separately:

For each lot of the training set mean values for each wavelength combination of wavelength excitation and wavelength emission were calculated and used for modeling. The mean value is encoded as e.g. M_Lot1_Mean.

Procedure and Rational for a Wavelength Selection for the BioView Sensor:

Out of 150 wavelength combinations only 120 were used. The wavelength selection may be based on the following rationale. According to fermentation experiments in bioreactors, where the BioView is used for monitoring, these signals do not seem to reflect any biogenic fluorophores as vitamins or amino acids. They more likely indicate the measurement environment as the surface of the container or catching up of environmental light. Therefore, the following wavelength combinations that are determined without spectral filters for excitation or emission are not used.

| exnd | emnd |
|---|---|
| no filter for excitation | no filter for emission |
| exnd/em310 | ex290/emnd |
| exnd/em330 | ex310/emnd |
| exnd/em350 | ex330/emnd |
| exnd/em370 | ex350/emnd |
| exnd/em390 | ex370/emnd |
| exnd/em410 | ex390/emnd |
| exnd/em430 | ex410/emnd |
| exnd/em450 | ex430/emnd |
| exnd/em470 | ex450/emnd |
| exnd/em490 | ex470/emnd |
| exnd/em510 | ex490/emnd |
| exnd/em530 | ex510/emnd |
| exnd/em550 | ex530/emnd |
| exnd/em570 | ex550/emnd |
| exnd/em590 | |

Principal Component Analysis of selected spectral fluorescence data calculated with 12 soy hydrolysate samples from the respective lots.

The following selected spectral fluorescence data are used for the Principal Component Analysis:

| | | | | | | |
|---|---|---|---|---|---|---|
| ex290/em330 | ex310/em350 | ex330/em370 | ex350/em390 | ex370/em410 | ex390/em430 | ex410/em450 |
| ex290/em350 | ex310/em370 | ex330/em390 | ex350/em410 | ex370/em430 | ex390/em450 | ex410/em470 |
| ex290/em370 | ex310/em390 | ex330/em410 | ex350/em430 | ex370/em450 | ex390/em470 | ex410/em490 |
| ex290/em390 | ex310/em410 | ex330/em430 | ex350/em450 | ex370/em470 | ex390/em490 | ex410/em510 |
| ex290/em410 | ex310/em430 | ex330/em450 | ex350/em470 | ex370/em490 | ex390/em510 | ex410/em530 |
| ex290/em430 | ex310/em450 | ex330/em470 | ex350/em490 | ex370/em510 | ex390/em530 | ex410/em550 |
| ex290/em450 | ex310/em470 | ex330/em490 | ex350/em510 | ex370/em530 | ex390/em550 | ex410/em570 |
| ex290/em470 | ex310/em490 | ex330/em510 | ex350/em530 | ex370/em550 | ex390/em570 | ex410/em590 |
| ex290/em490 | ex310/em510 | ex330/em530 | ex350/em550 | ex370/em570 | ex390/em590 | |
| ex290/em510 | ex310/em530 | ex330/em550 | ex350/em570 | ex370/em590 | | |
| ex290/em530 | ex310/em550 | ex330/em570 | ex350/em590 | | | |
| ex290/em550 | ex310/em570 | ex330/em590 | | | | |
| ex290/em570 | ex310/em590 | | | | | |
| ex290/em590 | | | | | | |
| ex430/em470 | ex450/em490 | ex470/em510 | ex490/em530 | ex510/em550 | ex530/em570 | ex550/em590 |
| ex430/em490 | ex450/em510 | ex470/em530 | ex490/em550 | ex510/em570 | ex530/em590 | |
| ex430/em510 | ex450/em530 | ex470/em550 | ex490/em570 | ex510/em590 | | |
| ex430/em530 | ex450/em550 | ex470/em570 | ex490/em590 | | | |
| ex430/em550 | ex450/em570 | ex470/em590 | | | | |
| ex430/em570 | ex450/em590 | | | | | |
| ex430/em590 | | | | | | |

For every data point 3 data points for each lot were used. In this example all lots were within the design space with mainly one principle component accounting for 95% of variation.

Results of the Nested ANOVA of the 12 Lots from the Training Set:

The ANOVA model shows that the overwhelming majority of the variance of the t[1]-values of the PCA model (89,81%) are caused by the different lots, whereas only 10,19% by the tube.

| Nested ANOVA: M1.t[1] versus Lot; Tube | | | | |
|---|---|---|---|---|
| Analysis of Variance for M1.t[1] | | | | |
| Source | DF | SS | MS | F | P |
| Lot | 11 | 7.73858E+06 | 703506.9070 | 27.441 | 0.000 |
| Tube | 24 | 615278.7509 | 25636.6146 | | |
| Total | 35 | 8.35385E+06 | | | |

| Variance Components | | | | |
|---|---|---|---|---|
| Source | Var | % of Comp. | Total | StDev |
| Lot | 225956.764 | 89.81 | 475.349 | |
| Tube | 25636.615 | 10.19 | 160.114 | |
| Total | 251593.379 | | 501.591 | |

| Expected Mean Squares | | |
|---|---|---|
| 1 | Lot | 1.00(2) + 3.00(1) |
| 2 | Tube | 1.00(2) |

Steps Applied for Model Building in SIMCA P+ Software as an Example:

The variables of Xs and Ys are defined in SIMCA P+ followed by a correlation of Xs to Ys and building of PLS models in SIMCA P+. After the scaling algorithms were applied (e.g. centering for fluorescence data and univariate scaling for the volumetric productivity parameter (process Y) first a PLS model with the selected spectra and relative volumetric productivity parameter units is built and evaluated in SIMCA P+. The resulting "Observed versus Prediction Plots" displays the predictive power of the first model.

Steps Applied for Model Evaluation in SIMCA P+:

The evaluation of model quality is done in SIMCA P+, whereby outliers and unusual data are removed from the data set. The "VIPs" are calculated in SIMCA P+ and evaluated. VIP values reflect the importance of terms in the model both with respect to process Y, i.e. volumetric productivity parameter of soy hydrolysate that corresponds in the present case to the manufacturing parameter of interest, i.e. its correlation to all the responses and with respect to X (in this example: wavelength combination). In the next step wavelength combinations with VIPs value≥1.0 are selected.

Steps of Re-modeling in SIMCA P+:

The new model was determined by using 12 VIP variables for re-modeling

Comparison of Models:

The comparison covers the parameters best model stability (Q2Y), most significant regression (p-value) at comparable data fit (R2Y). In this example the VIP model provides the best results for the criteria above.

Model Validation in SIMCA P+:

In this step the model was validated using 2D-fluorescence data of a new soy hydrolysate powder lot that was not used for model building so far is measured with the BioView sensor. The fluorescence and manufacturing data is imported as "prediction set" into SIMCA P+. Using the "VIP"-Model and fluorescence data of the new lot in SIMCA P+ the process Y (manufacturing parameter of interest) is calculated. Now the predicted process Y is compared to the process Y which was determined in the manufacturing process using SIMCA P +. Finally the "root mean square error of prediction" can be calculated in SIMCA P+ or the deviation between the predicted and determined process Y after a transfer of the data sets into excel.

Routine use of the Application:

For the proof of concept in routine application, the fluorescence spectrum of a new soy hydrolysate powder lot is measured. The fluorescence and manufacturing data are put into SIMCA P+ as "prediction set". The "VIP"-Model and fluorescence data of the new lot are used in SIMCA P+ to calculate the process Y parameter that is the volumetric productivity parameter (manufacturing parameter of interest). Based on the predicted result the lot is released for further applications. Based on the predicted values a preselection or assessment of the appropriate application of the new hydrolysate is done followed by optional additional testing in appropriate small scale cell culture cultivations for the intended use in manufacturing.

Obtaining Predictive Information Related to the volumetric Productivity Parameter by Determining Whether it Falls into a Predetermined Range:

In order to obtain the predictive information the following steps are applied: Setting an acceptable performance of a predetermined value of a manufacturing parameter of interest to be 100%, and determining whether the determined manufacturing parameter of interest obtained after said step is greater than 100% or not, wherein a performance of greater than 100% is a high performance and a performance of less than 100% is a low performance.

Finally, the lots are accepted that belong to the determined soy hydrolysate samples having a high performance and are further used as component in cell culture processes and cell culture media. The lots that belong to the determined soy hydrolysate samples having a low performance are rejected for use in further cell culture processes and cell culture media.

The invention claimed is:

1. A method for producing a recombinant target protein, comprising the steps of:
   (1) providing a plant or yeast hydrolysate having a high performance characteristic,
   (2) mixing the plant or yeast hydrolysate of step (1) with other cell culture medium components to form a cell culture medium or adding the plant or yeast hydrolysate of step (1) to a basal cell culture medium to form a cell culture medium,
   (3) providing one or more cells that produce the recombinant target protein,
   (4) culturing the one or more cells in the plant or yeast hydrolysate supplemented cell culture medium formed by step (2), such that the recombinant target protein is expressed and excreted from the cells into a culture supernatant, and recovering the recombinant target protein, wherein the high performance characteristic of the plant or yeast hydrolysate in powder form is predicted using a method comprising the steps of:
   a) providing a training set comprising a plurality of plant or yeast hydrolysate samples, each sample having a predetermined value of a manufacturing parameter of interest, b) irradiating a sample of said training set with light of a plurality of wavelengths in a predetermined range,
c) determining at least one measured value indicative of radiation emitted from the sample,
d) repeating steps b) and c) for all samples of said training set,
e) performing multivariate data analysis of the at least one measured value determined for each of the plurality of samples and corresponding predetermined manufacturing parameters of interest to obtain model parameters correlating the at least one measured value determined for each of the plurality of samples with the corresponding predetermined manufacturing parameters of interest,
f) obtaining information correlated to the manufacturing parameter of interest of a new sample different from the samples of said training set from at least one measured value indicative of radiation emitted from the sample according to step c) after irradiating said sample according to step b) by using those model parameters obtained in step e), and
g) obtaining predictive information related to the performance characteristic of the new sample by determining whether said manufacturing parameter of interest falls into a predetermined range.

2. The method according to claim 1, wherein the predetermined range of wavelengths of light lies within a range of 290 to 550 nm.

3. The method according to claim 1, further comprising the step of performing data processing of at least one measured value determined for each of the plurality of samples to obtain processed values, and using said processed values to perform multivariate data analysis in step e).

4. The method according to claim 1, wherein said predetermined range for obtaining predictive information related to the performance characteristic of said new sample by determining whether said manufacturing parameter of interest falls into it according to step g) comprises the following steps:
(i) setting an acceptable performance of a predetermined value of a manufacturing parameter of interest to be 100%, and
(ii) determining whether the determined manufacturing parameter of interest obtained after step f) is greater than 100%, wherein a performance of greater than 100% is a high performance and a performance of less than 100% is a low performance.

5. The method according to claim 1, wherein steps b) and c) comprise 2D-multiwavelength fluorescence spectroscopy analysis of the plant or yeast hydrolysate.

6. The method according to claim 1, wherein the plant hydrolysate is soy hydrolysate or wheat hydrolysate.

7. The method according to claim 1, wherein the manufacturing parameter of interest is determined on the basis of a cell culture and is selected from the group consisting of a volumetric productivity parameter, a virus titer and a cell number.

8. The method according to claim 1, wherein step e) further comprises data pre-processing and multivariate data analysis that is performed according to a validated chemometric model.

9. The method according to claim 8, wherein the data pre-processing comprises at least one of the following steps:
(iii) wavelength selection, and
(iv) scaling.

10. The method according to claim 8, wherein the validated chemometric model is calculated on the basis of the data as received from a pre-processing step further comprising the calculation of a chemometric model, the evaluation of said chemometric model, optionally the remodeling of the chemometric model by using specifically selected VIP-variables and the validation of the chemometric model with a new fluorescence data set obtainable from 2D-multiwavelength fluorescence analysis of a plant or yeast hydrolysate which performance is to be predicted.

11. A method for preparing a cell culture medium, comprising the steps of:
aa) providing a plant or yeast hydrolysate having a high performance characteristic as determined by the method according to claim 1, and bb) mixing the hydrolysate of step aa) with other cell culture medium components to form the cell culture medium or adding the plant or yeast hydrolysate of step aa) to a basal cell culture medium to form the cell culture medium.

12. The method according to claim 1, wherein the cell of step (3) is a CHO cell and the recombinant target protein is coagulation factor VIII, factor VII, factor IX, factor II, or factor X.

* * * * *